United States Patent [19]

Calzi et al.

[11] Patent Number: 4,980,538
[45] Date of Patent: Dec. 25, 1990

[54] HEATING AND TEMPERATURE-CONTROL DEVICE FOR BIOLOGICAL SAMPLE CONTAINERS

[75] Inventors: Claudio Calzi, Milan; Paolo Bonfiglo, Bareggio, both of Italy

[73] Assignee: Instrumentation Laboratory S. p. A., Milan, Italy

[21] Appl. No.: 363,123

[22] Filed: Jun. 8, 1989

[30] Foreign Application Priority Data

Jun. 10, 1988 [IT] Italy ............... 20929 A/88

[51] Int. Cl.$^5$ .................................. H05B 3/62
[52] U.S. Cl. .............................. 219/411; 219/388; 219/405
[58] Field of Search ............... 219/388, 405, 411, 502; 374/127, 132

[56] References Cited

U.S. PATENT DOCUMENTS

| | | | |
|---|---|---|---|
| 1,951,426 | 3/1934 | Littler | 374/127 |
| 2,438,160 | 3/1948 | Green | 219/502 |
| 2,860,225 | 11/1958 | Steen | 219/411 |
| 3,683,154 | 8/1972 | Kipple | 219/405 |
| 3,833,794 | 9/1974 | Moriyama | 219/502 |
| 3,916,152 | 10/1975 | Hinman | 219/389 |
| 4,135,883 | 1/1979 | McNeil et al. | 422/72 |
| 4,208,573 | 6/1980 | Risse | 219/411 |
| 4,259,866 | 4/1981 | sleighter | 374/127 |
| 4,441,015 | 4/1984 | Eichelberger | 219/411 |
| 4,708,886 | 11/1987 | Nelson | 422/72 |
| 4,738,825 | 4/1988 | Kelln et al. | 422/72 |

FOREIGN PATENT DOCUMENTS

| | | |
|---|---|---|
| 0160283 | 11/1985 | European Pat. Off. |
| 0172635 | 2/1988 | European Pat. Off. |
| 1103656 | 3/1961 | Fed. Rep. of Germany |
| 58421 | 11/1953 | France ............... 374/127 |
| 102312 | 12/1975 | German Democratic Rep. |
| 2147787 | 5/1985 | United Kingdom ........ 219/388 |

*Primary Examiner*—Teresa J. Walberg
*Attorney, Agent, or Firm*—Alan M. Doernberg

[57] ABSTRACT

A heating and temperature-control device for biological sample containers includes an assembly of lamps emitting infrared radiation within a wavelength of 1-5.5 micrometers and heating said containers by irradiation, and a sensor for infrared radiation of wavelength 7-14 micrometers which picks up the emission from the containers which derives from their heating. The signal obtained from said sensor is used to control the lamp emission in such a manner as to obtain the required container temperature and then keep it constant.

8 Claims, 2 Drawing Sheets

HEATING AND TEMPERATURE-CONTROL DEVICE FOR BIOLOGICAL SAMPLE CONTAINERS

BACKGROUND OF THE INVENTION

The present invention relates to devices for heating and controlling the temperature of containers, which containers are to be used for containing biological samples, especially for analysis purposes.

It is a well known fact that chemical analysis, and in particular the analysis of biological samples, must be carried out at a predetermined temperature to obtain correct results. In analysing small quantities of substance (such as the analysis of blood or other organic liquids with modern automatic analysis equipment) it is also important to heat not only the samples and reagents but also the small containers into which the samples and reagents are subsequently transferred to carry out the analysis. In this respect, if the samples and reagents are bought to a given temperature while in their storage containers and then transferred for analysis into small containers (such as the so-called rotors used in automatic analysis machines) not at the same temperature, it is apparent that because of the small mass of the samples and reagents (usually hardly more than droplets), they assume the temperature of the container and so give false analysis results.

To ensure that the required temperature is reached and remains constant with time, the containers containing the samples to be analysed are generally stored in storage equipment in the form of temperature-controlled ovens.

The problem common to such heating systems is that measuring the temperature inside the oven does not always give an exact indication of the temperature within the containers because of the inevitable thermal inertia.

In this respect, especially in the case of automatic machine analysis, withdrawing the containers from the oven only a short time after their insertion may mean that they have undergone insufficient heating. However if they are kept in for a time longer than that strictly necessary to obtain correct heating, and thus with a reasonable chance that the containers (which enter the oven not always at constant temperature) have reached the required temperature, there is a considerable slowdown in analysis rate. In addition, if conventional metods are used to measure the temperature of the interior of the oven and this is kept constant, thermal inertia again means that there can be no guarantee that the container temperature is maintained at constant value, and the containers can therefore leave the oven at the wrong temperature. The aforesaid problems could theoretically be solved by placing a temperature sensor in contact with the containers to obtain direct measurement of their temperature within the oven rather than the temperature of the oven interior itself. This method is however impracticable because any temperature sensor in contact with the containers would also be influenced by the oven internal tenperature which, as stated, is not always in constant relationship with the container temperature.

SUMMARY OF THE INVENTION the object of the present invention is to obviate the aforesaid drawbacks by providing a device and method for heating and temperature-controlling containers which allows their required temperature to be reached and maintained, and properly measured.

This object is attained by a heating and temperature-control device for biological sample containers, of the type comprisisng for said containers a heating chamber containing a plurality of infrared radiation heating sources and means for controlling the emission intensity of said plurality of sources, said means being governed by a sensor disposed within said chamber, characterised in that said sensor is a sensor for measuring the infrared radiation emitted by the containers in the chamber.

The novel principles of the present invention and its advantages over the known art will be more apparent from the description of one embodiment thereof applying said principles, which is given hereinafter with reference to the accompanying drawings.

DESCRIPTION OF THE PREFERRED EMBODIMENT

Figure 1:
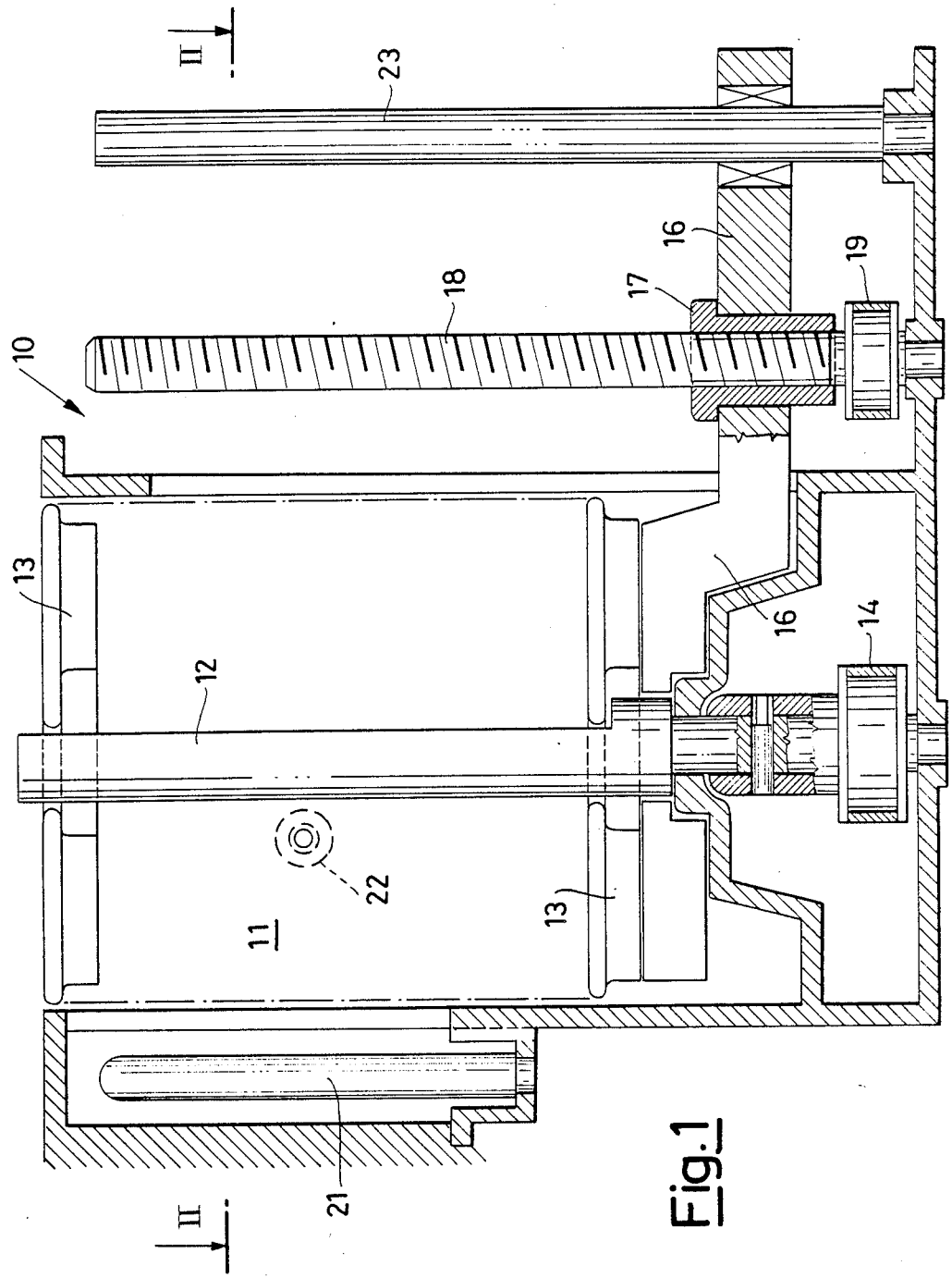
FIG. 1 is a diagrammatic sectional side elevation of a heating device constructed in accordance with the present invention.

With reference to the figures, a heating and temperature-control device 10 comprises a chamber 11 containing a vertical pin 12 connected by a belt 14 to an electric motor 15, and on which containers 13 in the shape of a circular ring with radial sectors, commoly known as rotors (of which only the first and last of the stack are shown for clarity in FIG. 1) for use in multiple automatic analysis equipment are stacked automatically of manually through an upper circular aperture in the chamber.

A horizontal arm 16 with one end placed below the lower rotor of the stack is mobile along a vertical guide 23 by means of a threaded sleeve 17 and a worm 18 parallel to it and connected by a belt 19 to an electric motor 20.

Figure 2:
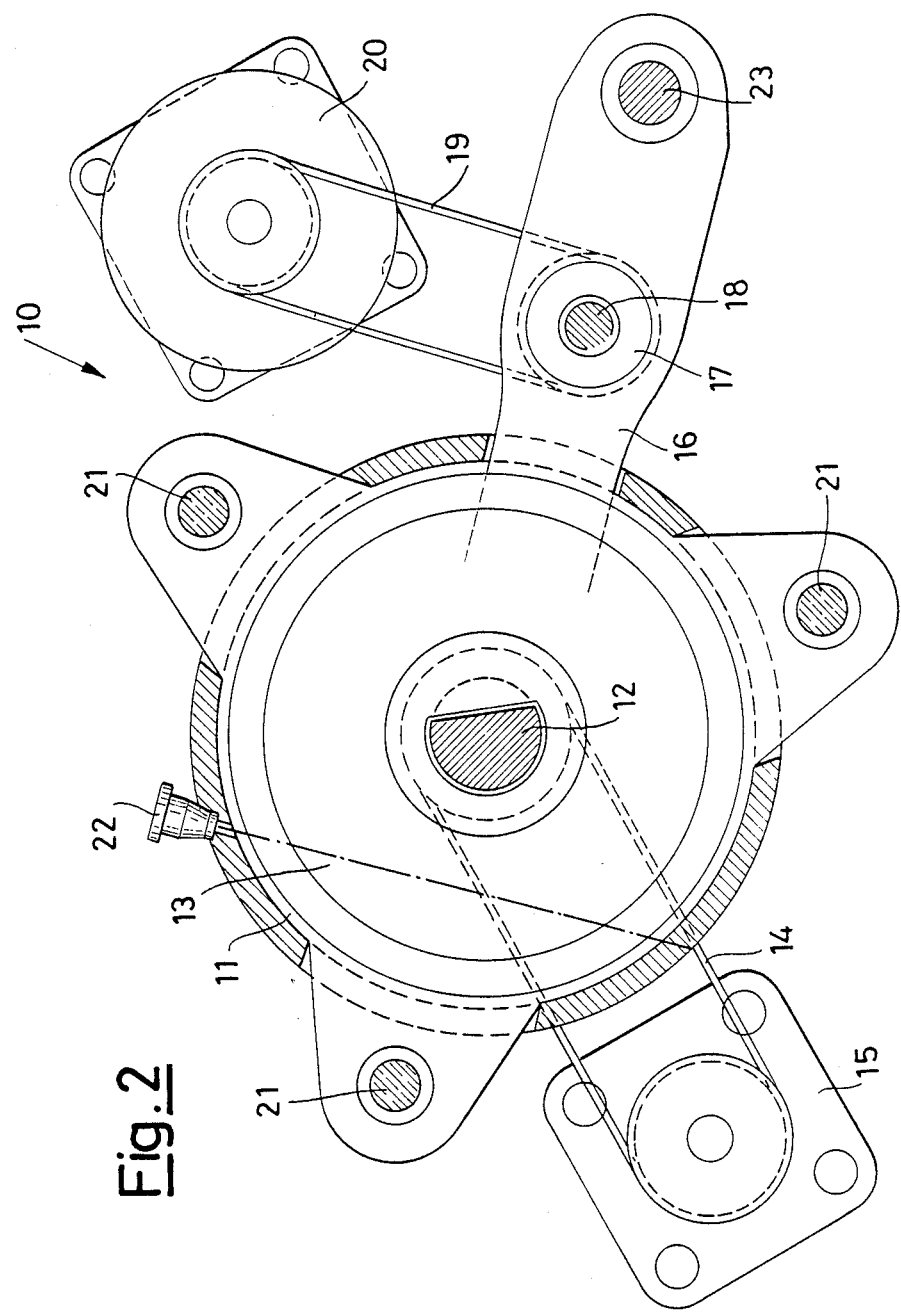
FIG. 2 is a section on the line II—II of FIG. 1.

Three infrared lamps 21 are disposed within the chamber 11 at the vertices of an ideal equilateral triangle centered on the pin 12 (as shown in FIG. 2) and parallel to the stack of rotors. An infrared sensor 22 is disposed (as shown in FIG.2) horizontally to face the stack of rotors along a direction which does not intersect the lamps 21.

The lamps 21 and sensor 22 are connected to a proportional control system of known type, which can be easily conceived by any expert of the art and is therefore not shown, neither are its connections.

It has been found that for the constituent material of the rotors (polymethacrylate), the best heating results are obtained for a wavelength of between 1 and 5.5 micrometers for the infrared radiation emitted by the infrared lamps. Good temperature sensitivity without source emission interference is obtained if the sensor is arranged to receive the emission from the rotor material within an infrared band of wavelength between 7 and 14 micrometers.

the operation of the device is as follows.

The rotors are initially mounted automatically or manually on the pin 12 through the upper aperture in the chamber 11 so that the lamps 21 irradiate them and heat them. By means of the motor 15, the pin 12 rotates the pile of rotors around the lamps to provide them with uniform irradiation and heating.

In accordance with a known physical law any heated body emits infrared radiation, the intensity of which is a function of the body temperature.

The sensor 22 picks up the infrared radiation of wavelength 7-14 micrometers emitted by the rotors as a consequence of the heating to which they are subjected, the resultant signal being used by said control system to control the emission entensity of the lamps 21.

As the intensity of the infrared radiation emitted by the rotors is a function of their temperature, measuring of this intensity provides the necessary feedback to the control system, in order to keep the rotor temperature constant after if has been brought to the required value.

The fact that the emission wavelength of the infrared lamps and the wavelength of the received return emission from the rotors are different is of primary importance for non-interference between said temperature and the lamp temperature in the rotor temperature measurement.

This therefore enables the true temperature of the rotors to be indirectly measured moment by moment during their heating, so making it possible to attain the required temperature in the shortest possible time with very high precision and constancy. Having attained the required temperature (reliably measured by the described method), when the individual rotors are required for the analysis procedure the motor 20 raises by means of the worm 18 the arm 16 supporting the stack of rotors, so making the first rotor of the stack emerge from the top of the chamber 11 so that it can be withdrawn (for example automatically by an analysis machine) for immediate use.

Usually it is possible to load reagents and samples into the cuvettes of the top rotor while it is on the stack, but the top rotor can also be removed from the stack empty.

The described embodiment of the present invention is given by way of example only, and is not to be considered limitative of its scope.

It is apparent that the containers can be of any form as can be the system for handling them within the device, and in addition the heating lamps and the sensor measuring the infrared emission from the containers can be of different arrangement.

We claim:

1. A heating and temperature-control device for biological sample containers in the shape of a circular ring with a plurality of radial compartments and a central aperture, the device comprising:
   (a) a cylindrical heating chamber,
   (b) a vertical pin located in the cylindrical heating chamber such that the containers can be stacked in the cylindrical heating chamber with the central aperture of each container mounted on the vertical pin,
   (c) a plurality of infrared radiation heating sources,
   (d) means for controlling the emission intensity of said plurality of infrared radiation heating sources on the containers in the cylindrical heating chamber, and
   (e) sensor means for measuring the infrared radiation emitted by containers in the chamber and governing said means for controlling.

2. A device as claimed in claim 1, characterised in that said plurality of sources emits infrared radiation having a wavelength within a first predetermined band, said sensor means having its maximum sensing sensitivity within a second predetermined band, said two bands being separated.

3. A heating device as claimed in claim 2, characterised in said first predetermined band is 1 to 5.5 micrometers.

4. A heating device as claimed in claim 2, characterised in that the second predetermined band is 7-14 micrometers.

5. A heating device as claimed in claim 1, characterised in that said sensor means is disposed such that its sensing line does not intersect with any of the plurality of infrared radiation heating sources.

6. A heating device as claimed in claim 1, characterised in that said vertical pin is connected to motorized means for its rotation about its axis.

7. A heating device as claimed in claim 1, characterised in that in said chamber there are provided means for moving said containers towards an outlet aperture in the chamber.

8. A heating device as claimed in claim 1, characterised in that said sources are three in number and are disposed at the vertices of an equilateral triangle centered on the vertical axis of the chamber.

* * * * *